(12) United States Patent
Warburton

(10) Patent No.: US 8,486,106 B2
(45) Date of Patent: Jul. 16, 2013

(54) DISPOSABLE DIGITAL TOURNIQUETS AND RELATED METHODS OF PROVIDING OCCLUSION PRESSURES TO A SINGLE DIGIT DURING SURGICAL PROCEDURES

(75) Inventor: Mark Joseph Warburton, High Point, NC (US)

(73) Assignee: Piper Medical, Inc., High Point, NC (US)

( * ) Notice: Subject to any disclaimer, the term of this patent is extended or adjusted under 35 U.S.C. 154(b) by 760 days.

(21) Appl. No.: 11/222,956

(22) Filed: Sep. 9, 2005

(65) Prior Publication Data

US 2006/0089668 A1   Apr. 27, 2006

Related U.S. Application Data

(60) Provisional application No. 60/620,817, filed on Oct. 21, 2004.

(51) Int. Cl.
*A61B 17/00* (2006.01)

(52) U.S. Cl.
USPC ........................................ 606/203

(58) Field of Classification Search
USPC ............. 606/201, 202–203, 74; 24/68 R, 24/69 R, 70 ST, 69 ST, 71 R, 71 T, 71 ST, 24/115 R, 132 R, 133, 134 R
See application file for complete search history.

(56) References Cited

U.S. PATENT DOCUMENTS

| | | | | |
|---|---|---|---|---|
| 3,402,435 A | * | 9/1968 | Merser ...................... | 24/16 PB |
| 3,514,810 A | | 6/1970 | Westergren | |
| 3,717,906 A | * | 2/1973 | Wells ...................... | 24/16 PB |
| 3,816,878 A | * | 6/1974 | Fulton et al. .............. | 24/16 PB |
| 4,272,047 A | * | 6/1981 | Botka ........................ | 248/74.3 |
| 4,429,699 A | * | 2/1984 | Hatschek .................... | 600/494 |
| 4,516,576 A | * | 5/1985 | Kirchner .................... | 606/203 |
| 4,635,635 A | * | 1/1987 | Robinette-Lehman ....... | 606/202 |
| 4,760,846 A | | 8/1988 | Mers Kelly et al. | |
| 4,770,175 A | * | 9/1988 | McEwen ...................... | 606/203 |
| 5,031,943 A | * | 7/1991 | Scott et al. ................ | 292/307 R |
| 5,102,075 A | * | 4/1992 | Dyer .............................. | 248/61 |
| 5,129,511 A | * | 7/1992 | Brown et al. ................ | 206/63.3 |
| 5,168,863 A | * | 12/1992 | Kurtzer ........................ | 600/122 |
| 5,452,523 A | * | 9/1995 | Jansen ........................ | 33/555.4 |
| 5,658,298 A | * | 8/1997 | Vincent et al. .............. | 606/139 |
| 5,690,672 A | * | 11/1997 | Cohen .......................... | 606/203 |
| 5,704,097 A | * | 1/1998 | Rahav ........................ | 24/16 PB |
| 5,715,578 A | * | 2/1998 | Knudson .................... | 24/16 PB |
| 5,873,814 A | * | 2/1999 | Adair ........................... | 600/109 |

(Continued)

FOREIGN PATENT DOCUMENTS

| | | | | |
|---|---|---|---|---|
| DE | 3150751 A | * | 6/1983 | |
| GB | 2081584 A | * | 2/1982 | |

OTHER PUBLICATIONS

McEwen et al., *New finger cuffs for use with digital tourniquets*, J. Hand Surg 1988: 13A: 888-892.

(Continued)

*Primary Examiner* — Gary Jackson
*Assistant Examiner* — Jonathan Hollm
(74) *Attorney, Agent, or Firm* — Myers Bigel Sibley & Sajovec, P.A.

(57) ABSTRACT

A single-use disposable digital tourniquet includes a generally rigid support body comprising first and second spaced apart cuff channels sized and configured to receive a cuff therethrough.

44 Claims, 14 Drawing Sheets

U.S. PATENT DOCUMENTS

| | | | | |
|---|---|---|---|---|
| 5,873,890 A | * | 2/1999 | Porat | 606/201 |
| 5,893,870 A | * | 4/1999 | Talen et al. | 606/201 |
| 5,964,013 A | * | 10/1999 | Bergstrom | 24/16 PB |
| 6,053,169 A | * | 4/2000 | Hunt | 128/876 |
| 6,192,554 B1 | * | 2/2001 | Dumcum | 24/16 PB |
| 6,530,126 B2 | * | 3/2003 | Caveney et al. | 24/16 PB |
| 6,899,720 B1 | * | 5/2005 | McMillan | 606/203 |
| 6,960,223 B1 | * | 11/2005 | Ambach | 606/203 |
| 2005/0070933 A1 | * | 3/2005 | Leiboff | 606/153 |
| 2005/0113866 A1 | * | 5/2005 | Heinz et al. | 606/203 |
| 2006/0025728 A1 | * | 2/2006 | Leiboff et al. | 604/317 |

OTHER PUBLICATIONS

Tountas, *A disposable pneumatic digital tourniquet*, J. Hand Surg 1986: 11A: 600-601.

* cited by examiner

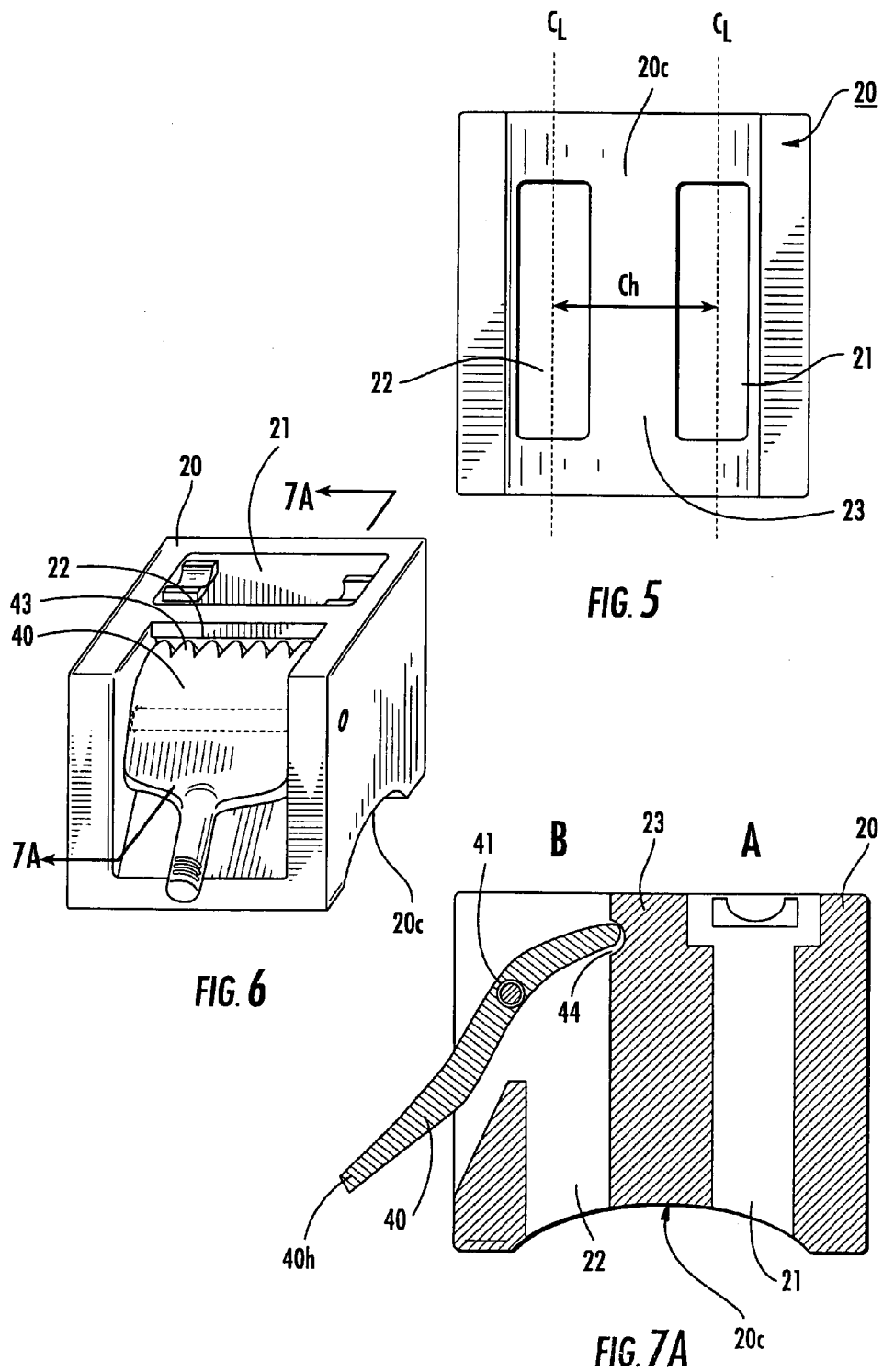

DISPOSABLE DIGITAL TOURNIQUETS AND RELATED METHODS OF PROVIDING OCCLUSION PRESSURES TO A SINGLE DIGIT DURING SURGICAL PROCEDURES

RELATED APPLICATIONS

This application claims priority to U.S. Provisional Application Ser. No. 60/620,817, filed Oct. 21, 2004, the contents of which are hereby incorporated by reference as if recited in full herein.

FIELD OF THE INVENTION

This invention relates to digital tourniquets for use in medical procedures.

BACKGROUND OF THE INVENTION

Injuries to the middle and terminal (end) portions of the thumb and other hand digits are relatively commonplace, with the number of treatment procedures for these types of injuries believed to number in the thousands per day in the United States alone. Examples of such injuries include lacerations, abrasions, avulsions, crush injuries, fractures, burns, and even partial amputations. The types of physicians and surgeons treating these types of injuries can include primary care physicians, emergency medicine physicians, general surgeons, plastic surgeons, trauma surgeons and orthopedic surgeons in offices, hospital operating rooms, emergency rooms, and even urgent care clinics.

Conventionally, a patient is given an anesthetic that can include a digital or regional block and/or a local anesthetic with LIDOCAINE or MARCAINE®. The hand and fingers are prepped and draped. A sterile rubber band(s) or Penrose drain (which is a thin-walled rubber tube) is used to stop arterial blood flow to the affected digit. This is done by wrapping the rubber band or Penrose drain around the proximal volar (palm) surface of the digit and clamping with a hemostat. When the procedure is complete, the hemostat is unclamped and arterial blood flow is restored.

Unfortunately, both the rubber band and the Penrose drain have a tendency to roll up as they are stretched axially, which can apply increased pressure on the finger or thumb as the surface area over which the force is applied decreases (it may be described as being similar to a wire being wrapped about the finger or thumb). In addition, use of these types of tourniquets may be such that the external pressure applied to the finger or thumb is not well controlled and may be excessive or beyond the pressure required to stop arterial blood flow. Unfortunately, when excessive pressure is applied to a small region, tissue and/or nerve damage can occur, particularly during relatively lengthy procedures.

In addition, other factors are influencing hand surgery that question the suitability of conventional digital tourniquets. For example, the population is aging and older patients tend to have tissue with atherosclerotic arteries that may be able to withstand less external pressure compared to a younger patient's tissue. In addition, health care costs are rising and more surgeries are being done in an outpatient or office setting, which are less likely to have access to specialized (costly) equipment. This trend may result in more local and digital blocks being used to treat injuries to the digit, which will likely increase the use of digital tourniquets.

In view of the foregoing, there remains a need for digital tourniquets that can provide sufficient occlusion pressure in an easy-to-use and economic manner.

SUMMARY OF EMBODIMENTS OF THE INVENTION

Certain embodiments of the present invention provide single-use disposable digital tourniquets that include a generally rigid support body comprising first and second spaced apart cuff channels sized and configured to receive a cuff therethrough.

In some embodiments, the digital tourniquets can have a first (digit contacting) surface with a curvilinear profile. The first surface can include a generally medial support region (that may be at the most depressed portion of the first surface) disposed intermediate the first and second cuff channels.

The tourniquets may also include two spaced apart cuff channels and an anchoring member configured to hold a first end portion of a cuff in the support body first channel and a clamping member configured to hold a spaced apart portion of the cuff proximate the second channel. In operation, the anchoring and clamping members can cooperate with the support body to provide a cuff with a nearly closed figure (such as an open ended loop) at a desired tension over a digit held on the support body.

In particular embodiments, the tourniquets can include a deformable member configured to operatively communicate with the cuff. The deformable member may be configured to automatically yield or break when the cuff is tensioned above a target threshold amount to provide a tactile and/or audible alert to a clinician that a target occlusion pressure has been achieved.

Embodiments of the present invention provide single-use disposable manually operated digital tourniquets that a physician or surgeon can relatively easily operate (typically without requiring assistance).

Other embodiments are directed to digital tourniquets that include: a generally rigid support body comprising first and second spaced apart cuff channels, wherein the support body comprises a first surface that, in position, contacts a target digit; and a planar non-inflatable elastomeric cuff that is slidably insertable through the first and second channels of the support body so as to extend through the first channel away from the first surface and into the second channel to provide a cuff with a curvilinear portion that extends outward from the support body first surface.

The cuff can include opposing first and second end portions. The first end portion can include a rod channel extending thereacross and a rod held therein with opposing end portions of the rod extending beyond the bounds of the cuff.

In some embodiments, the cuff can comprise a planar elastomeric material that is sized and configured to maintain its width dimension and resist roll-up in an operative (stretched) configuration.

In some embodiments, the tourniquets can be selectively used by a clinician in either orientation selected by the clinician, i.e., allowing a clamping portion to be located proximate a thumb of a patient irrespective of the affected hand.

Other embodiments are directed to kits of digital tourniquets providing for a range of different occlusion pressures. The kits include: (a) a first digital tourniquet generally rigid support body having first and second cuff channel lengths sized to accommodate a cuff having a first width; and (b) a second digital tourniquet generally rigid support body having first and second cuff channel lengths sized to accommodate a cuff having a second width that is greater than the first digital tourniquet cuff first width.

In some embodiments, the kit can also include first and second generally planar elastomeric cuffs, one having a first cuff width configured for insertion into the first support body and the other having a second cuff width that is greater than the first cuff width and is configured for insertion into the second support body. The different support bodies and associated cuffs can be configured to provide increased reliability for different preferential occlusion pressures so that a clinician can select the appropriate body/cuff in situ at a point of surgery.

Other embodiments are directed to kits of non-inflatable cuffs that include a plurality of elongate non-inflatable cuffs of different widths, each cuff having an end portion with a channel configured to accept a rod thereacross.

The foregoing and other objects and aspects of the present invention are explained in detail in the specification set forth below.

BRIEF DESCRIPTION OF THE DRAWINGS

FIG. 5 is a top view of the support body shown in FIG. 4.

FIG. 6 is a side perspective view of the device shown in FIG. 3.

FIG. 7A is a cross-sectional view taken along line 7-7 in FIG. 6.

DESCRIPTION OF EMBODIMENTS OF THE INVENTION

Figure 1:
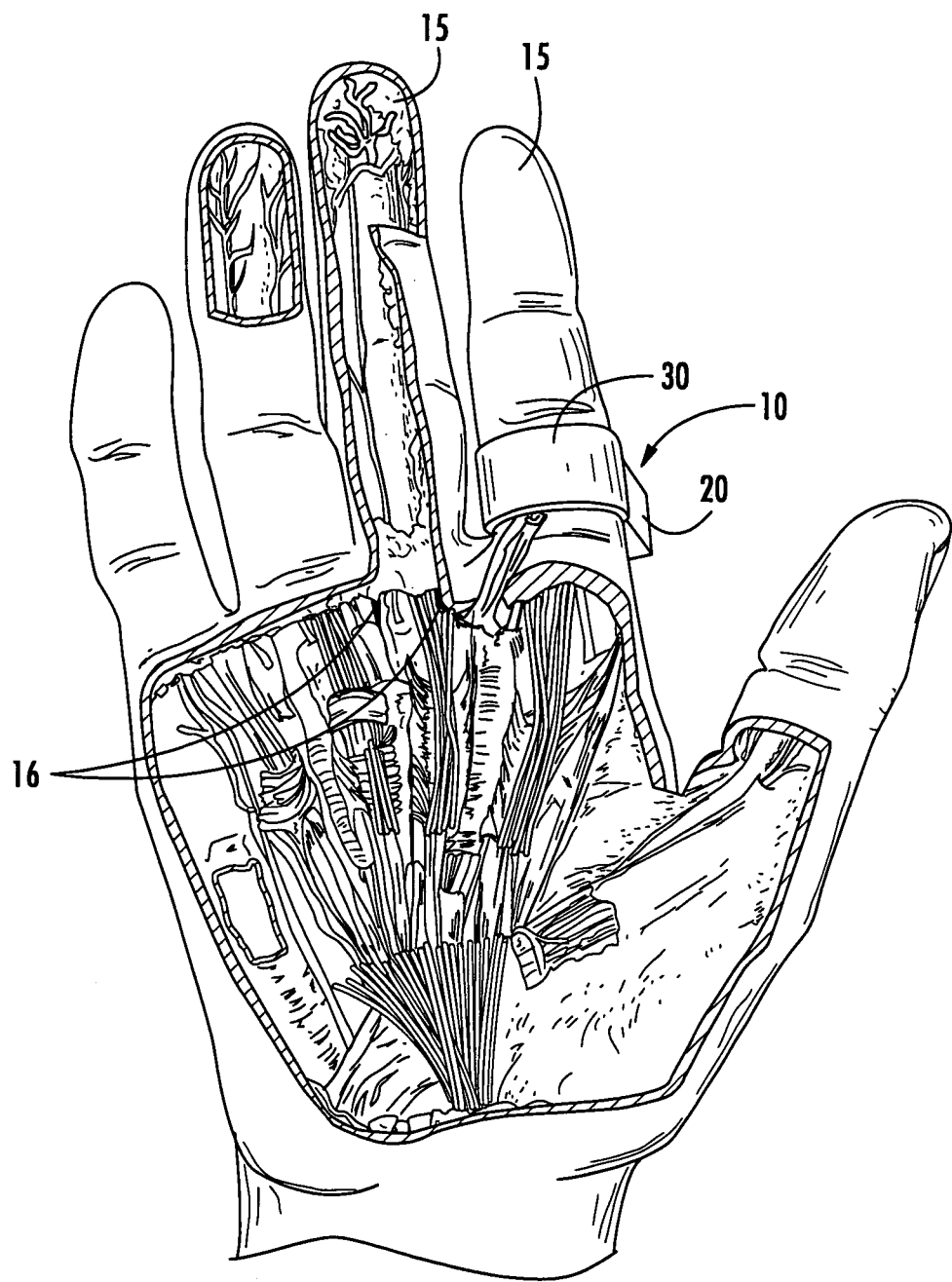
FIG. 1 is an anatomical drawing of the hand with some of the skin and superficial fascia removed to expose the two neurovascular bundles, each having one artery and one nerve, and an exemplary digital tourniquet according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and should not be interpreted in an idealized or overly formal sense unless expressly so defined herein. The word "cuff" means a flexible band and/or strip of material configured to apply pressure to a target region of a digit. The words "digital" or "digit" refers to an anatomical member, i.e., a hand digit describes a thumb and/or a finger, and a foot digit describes a toe. The term "polymer" includes copolymers and derivatives and/or combinations thereof. The members 20, 30 can comprise a generally rigid elastomeric material. The phrase "generally rigid" means that the body may flex somewhat but is structurally sufficiently rigid to maintain its shape during normal use when the other components are assembled thereto.

Figure 2A:
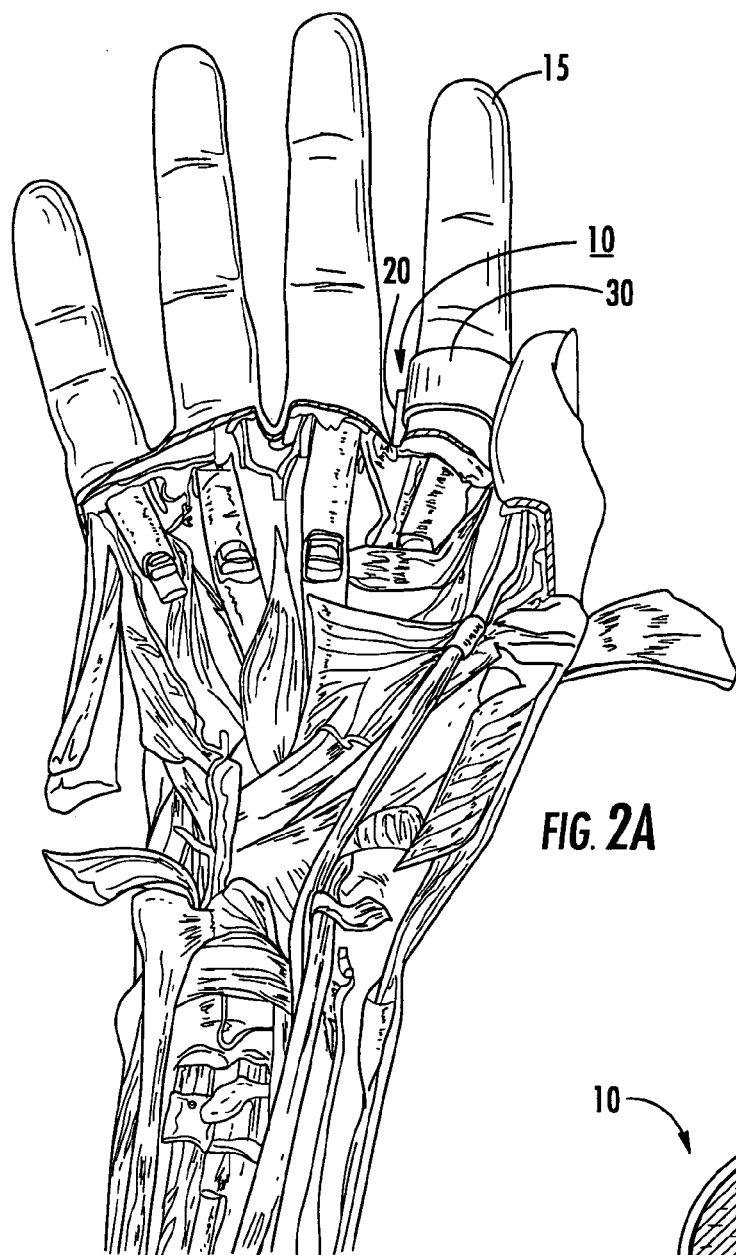
FIG. 2A is an anatomical drawing of the hand also illustrating the two neurovascular bundles and the proper palmar digital arteries with an exemplary digital tourniquet in position according to embodiments of the present invention.
Figure 2B:
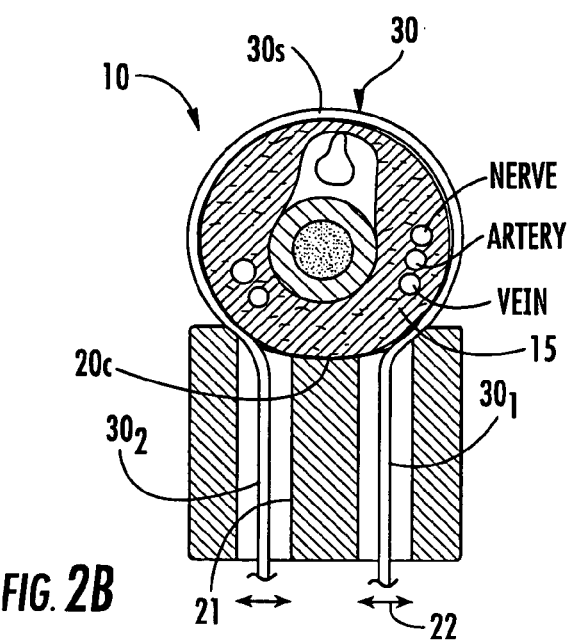
FIG. 2B is a cross-sectional view of an exemplary digital tourniquet in one position according to embodiments of the present invention.

Referring to FIG. 1, a digital tourniquet 10 is shown on a hand digit 15. As shown in FIG. 1, a digit 15 includes two neurovascular bundles 16, and, as known to those of skill in the art, each bundle 16 includes one artery and one nerve that extends from the hand to the tip of the finger. As shown, the digital tourniquet 10 includes a support body 20 and a cuff 30 that cooperate to apply occlusion pressure to the digit 15 undergoing treatment. FIG. 2A illustrates the tourniquet 10 on a hand with a partial dissection of the palm to illustrate anatomical features. FIG. 2B illustrates a partial section view of the tourniquet 10 in an exemplary position with respect to a cross-section of a finger and illustrating a nerve, artery and vein (palmar digital).

FIG. 2B also illustrates that the support body 20 includes a digit contact surface 20c and first and second spaced apart cuff channels 21, 22. The channels 21, 22 can be configured to extend generally orthogonal to a plane extending across the contact surface 20c and/or with respect to the digit 15 being treated. In position in the support body 20, the cuff 30 is configured as a closed perimeter segment 30s above the support body 20. That is, the closed perimeter segment 30s extends above the digit contact surface 20c and opposing cuff sides $30_1$, $30_2$ are configured to enter and extend through a respective one of the first and second channels 21, 22. The cuff 30 is pulled to tighten cuff segment 30s and cause the segment 30s to exert occlusion pressure against the digit 15.

In some embodiments, a first side of the cuff $30_1$ is secured to the body 20, typically inside or proximate the first channel 21. The cuff 30 is then directed to travel above the contact surface 20c and travel through the second channel 22. A length of the second side of the cuff $30_2$ typically extends beyond the bounds of the support body 20 out of the second channel 22. In use, a clinician can pull the second side of the cuff $30_2$ to tension the cuff and apply occlusion pressure to the digit 15.

Figure 2C:
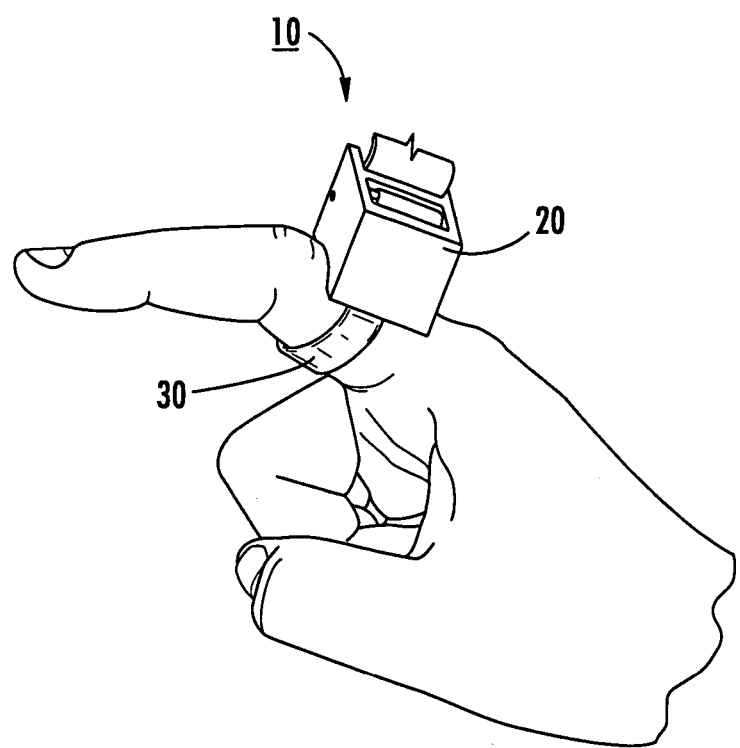
FIG. 2C is a perspective view of an exemplary digital tourniquet about a proximal phalanx portion of a digit according to embodiments of the present invention.
Figure 2D:
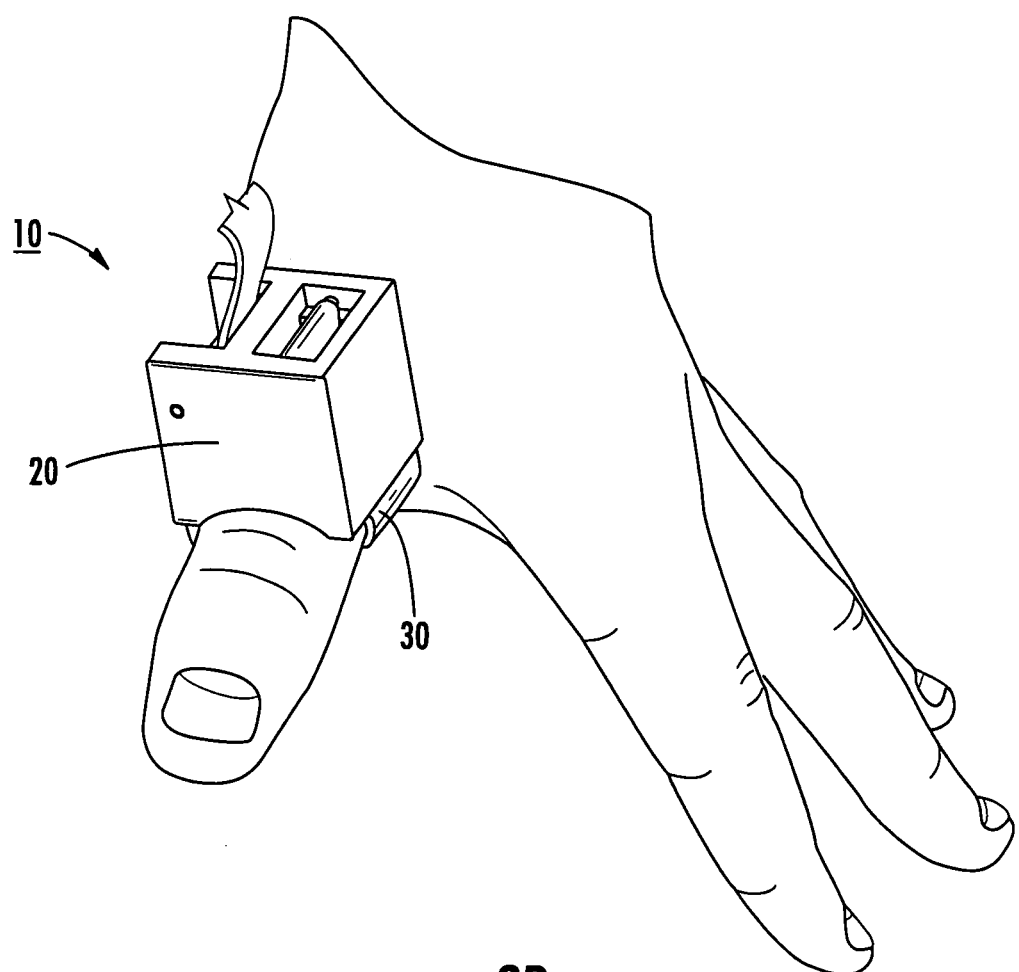
FIG. 2D is a perspective view of the digital tourniquet about a proximal phalanx portion of a thumb according to embodiments of the present invention.

FIGS. 2C and 2D illustrate that in some embodiments, the tourniquet 10 can be positioned about a proximal phalanx portion of a digit. FIG. 2C illustrate an exemplary position of the device 10 on a finger and FIG. 2D illustrates an exemplary position of the device on a thumb. It is contemplated that the device 10 can be used at a number of suitable locations on a digit including for surgery on either the dorsal or volar surface, although conventionally the device may be used dorsally over the proximal phalanx as shown, for example, in FIGS. 1, 2C and 2D.

FIGS. 3-7 illustrate one embodiment of a support body 20. As shown, the support body 20 has a curvilinear digit contact surface 20c. The contact surface 20c may have a shallow or low profile such that the digit is held substantially exposed and accessible (relatively unimpeded) to a clinician. The term "shallow" typically means that the profile has a depression that is less than about 5 mm (for most adult uses). Pediatric tourniquet support bodies 20 may have a profile with a shallower dimension, such as less than about 3 mm.

Figure 3:
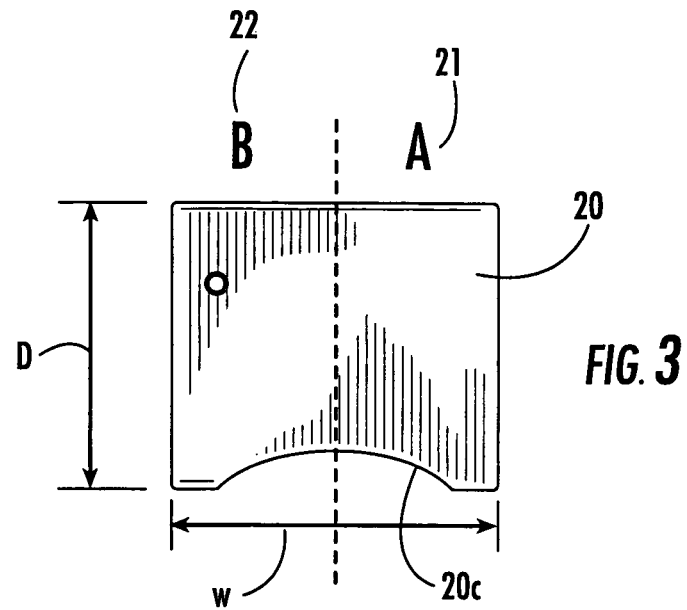
FIG. 3 is an end view of one embodiment of a digital tourniquet support body according to embodiments of the present invention.
Figure 4:
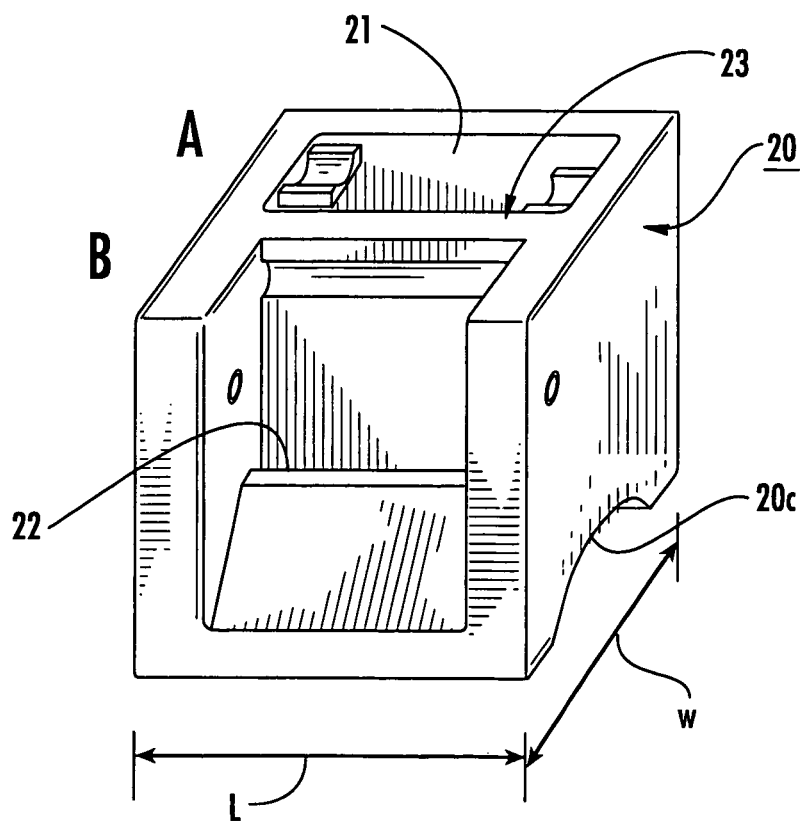
FIG. 4 is a side perspective view of the support body shown in FIG. 3.

FIGS. 3 and 7 illustrate that the contact surface 20c may be generally arcuate and correspond to a profile of a portion of a digit to allow the support body to more conformally fit against the target digit region in use. For example, the curvilinear contact surface 20c can be configured so that a digital midline of the digit being treated resides beyond (typically above) the bounds of the support body 20 when resting thereon. The body 20 can include first and second sides, A, B, respectively. The first channel 21 can be disposed on the first side A and the second channel 22 can be disposed on the second side B. A medial segment 23 can extend between and separate the first and second channels 21, 22. FIG. 4 shows that the medial segment 23 can be generally closed partition or body portion that can generally extend at least a major portion (or even entire) the thickness or depth dimension "D" of the body 20. Typically, the medial segment 23 defines at least a portion of the digit contact surface 20c as shown in FIG. 5. The first side A may provide an anchoring function and the second side B may provide a clamping function as will be discussed further below. However, the invention is not limited thereto as the locations of the components and/or functions may be interchanged for certain embodiments.

The width W (FIG. 4) of the support body 20 can be configured to generally correspond with a width of a digit being treated. In other embodiments, the width of the support body 20 may be lesser or greater than that of the digit being treated. The spacing of the channels 21, 22 can be configured relative to each other so that the cuff 30 when attached and/or assembled to the support body 20 is able to generate the desired cuff pressure/configuration. The channels 21, 22 can be aligned and extend generally parallel in the depth dimension D. The channels 21, 22 can be closely spaced in the width direction to allow the cuff segment 30s to form an open loop turn 30t (FIG. 11A) that defines the closed perimeter segment 30s above the digit contact surface 20c.

In particular embodiments, as shown in FIG. 3, the support body 20 can be generally square about the axial and sagittal directions (L×W dimensions). The digit contact surface 20c can be configured to define a concave surface that contacts the target surface of the digit, which generally conforms with the finger (i.e., the contact surface 20c may conform dorsally, volarly, and/or otherwise with the target placement). This configuration allows the body 20 to rest on the top (dorsum) of the finger. Other mounting configurations and orientations of the support body 20 relative to the digit may also be used.

In some embodiments, as shown in FIG. 5, the centerlines of the channels 21, 22 are spaced apart in the width direction between about 1-20 mm, typically between about 2-12 mm, and more typically between about 2-8 mm. During use, at the location the cuff exits the first channel 21 and enters the second channel 22, the cuff 30 can rest against the outermost edge of the respective channel at the contact surface 20c. That is, the cuff 30 exits the first channel 21 and travels laterally outward a distance to wrap about the digit then travels laterally inward and into the second channel 22. The spacing distance of the channels 21, 22 may vary depending on the target treatment digit and age and gender of the patient. Typically, the spacing of the channels 21, 22 is such that they reside less than the width of a digit being treated so that the cuff segment 30s is able to wrap about a greater side area of the digit proximate the contact surface of the support body 20c and is sized so as not to pinch the skin on the digit (on the dorsum of the finger) of the patient. In some embodiments, the width of the medial segment 23 at the contact surface 20c may define the separation distance of the channels as shown in FIG. 5.

The length L (FIG. 4) of the support body 20 can be sized to be about the same, or more typically, a small amount larger than the length of the channels 21, 22 and/or width of the cuff 30. The support body 20 can be a generally rigid lightweight body. The support body 20 can be single-use disposable or sterilized for re-use. The cuff 30 is typically single-use disposable. In some embodiments, the support body 20 is a generally rigid elastomeric body. In some embodiments, the support body 20 is a molded polymer body.

Figure 7B:
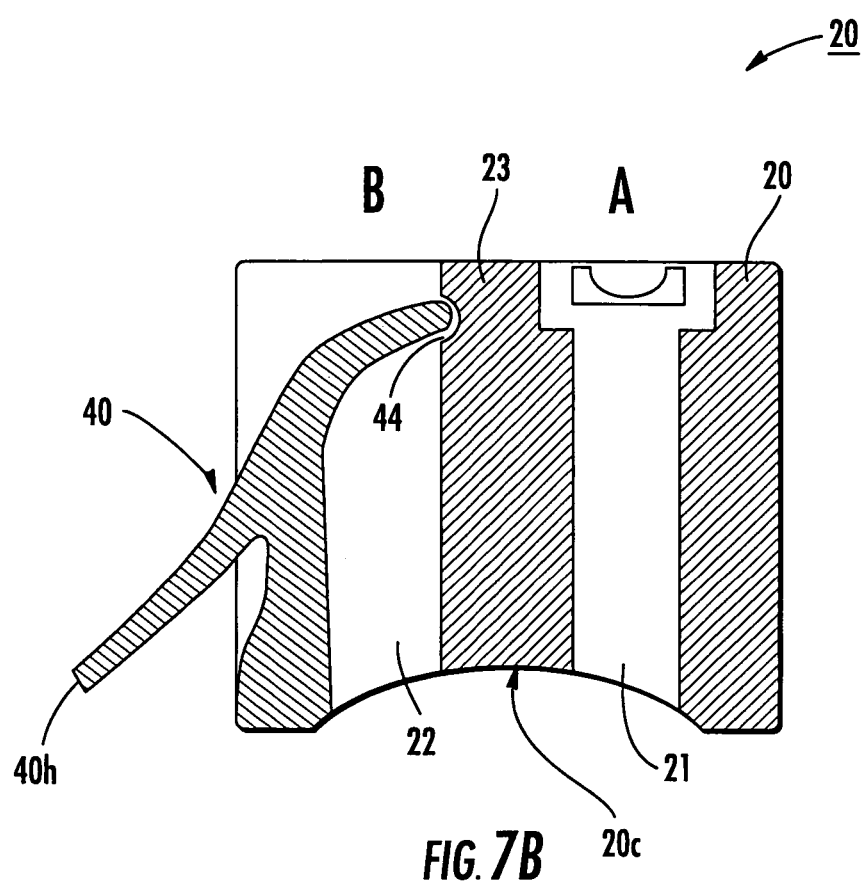
FIG. 7B is a cross-sectional view of a different embodiment of the support body having an integrally molded anchor portion according to alternate embodiments of the present invention.
Figure 8:
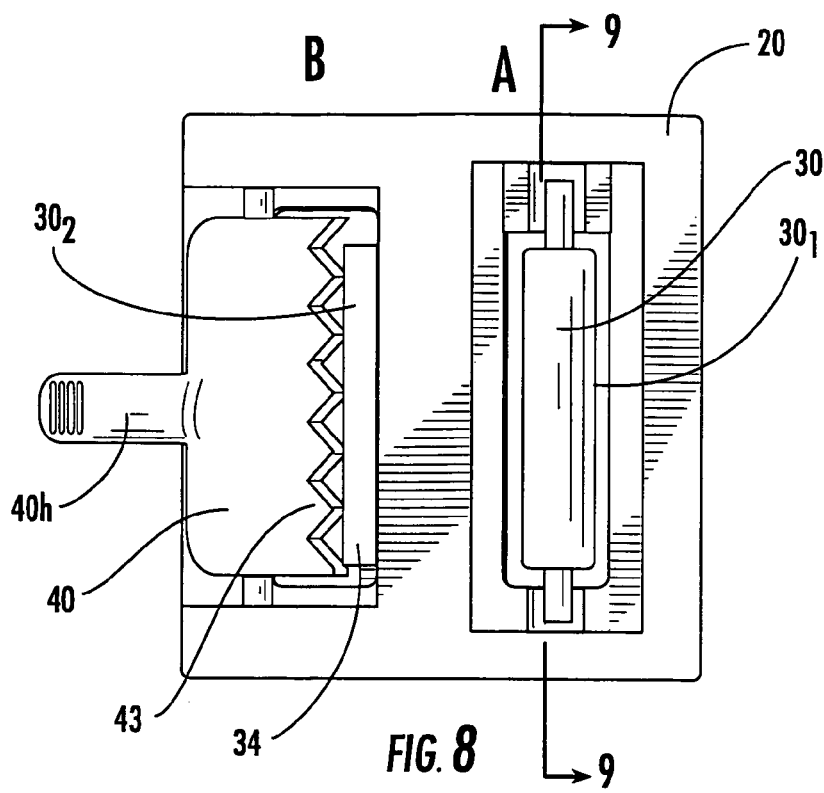
FIG. 8 is a bottom view of the device shown in FIG. 5.
Figure 9:
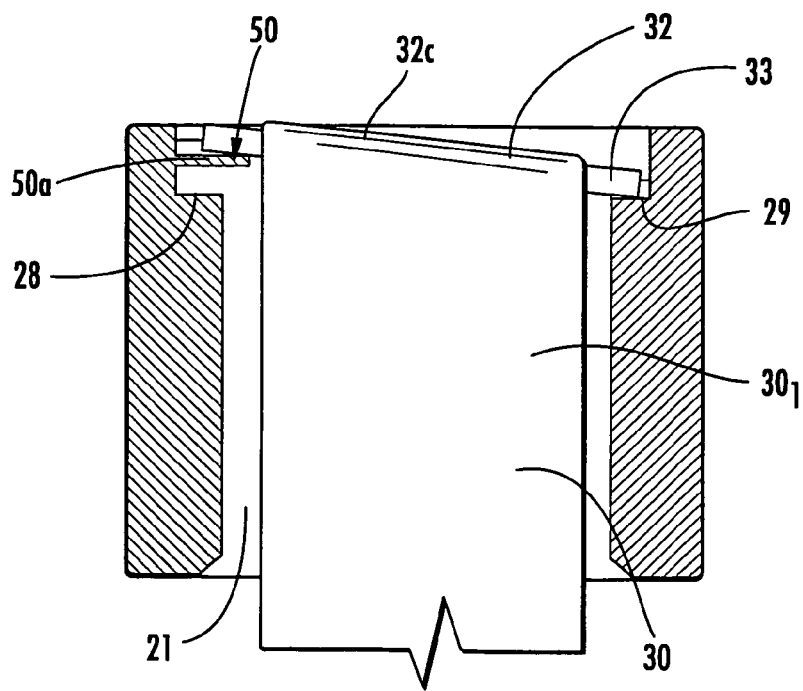
FIG. 9 is a cross-sectional view of the device shown in FIG. 8 taken along line 9-9 and illustrating a deformable projection according to embodiments of the present invention.

In certain embodiments, the support body 20 can include an anchoring side and a tension adjusting side B. Typically, as shown in FIGS. 4, 7 and 8, the anchoring side is proximate and/or in the first channel 21 while the tension adjusting side is downstream of the second channel 22. In some embodiments, a first end portion of the cuff 32 (FIGS. 9 and 10) can be configured with a rod channel 32c that is sized and configured to receive a rod 33 thereacross. The rod 33 engages the support body 20 and anchors the first end portion of the cuff 32 to the support body 20. As shown in FIG. 9, in some embodiments, the channel 21 can include spaced apart retaining shoulders 28, 29 that project a distance across the channel 21 and hold the first end portion of the cuff 32 via the rod 33 in position in the body 20 during use. The shoulder 29 and/or corresponding end portion of the rod 33 can be configured to inhibit sliding. For example, the shoulder 29 and/or rod end 33 can have an increased friction coating or layer, such as a flexible adherent. The other shoulder 28 and/or opposing end of the rod 33 may also include such a material. The rod and cuff 33, 30 can be slidably attached and/or removed from the support body 20 before and/or after use. The tourniquet 10 can be single-use disposable.

The second end portion of the cuff 34 extends beyond the bounds of the support body 20 and allows a clinician to easily access the cuff to pull the cuff to a desired tension at which time the cuff can be secured against the body 20. Typically, the cuff 30 is secured to the support body 20 using an integral clamping device 40. FIG. 4 illustrates the support body 20 without a clamping device. As shown in FIG. 7A, the clamping device 40 can be configured with a pivot 41. The clamping device 40 can be biased to pivot toward the support body medial segment 23 to apply a clamping force sufficient to hold the cuff at a desired tension and/or occlusion pressure. During use, a clinician can push a handle 40h to pivot the clamping device 40 away from the support body 20. When a desired occlusion pressure is reached, a clinician can release the handle 40h, allowing the clamping device 40 to return to its biased closed configuration to pinch the cuff 30 against the support body 20. The clamping device 40 can include a serrated or teeth forward edge portion 43 (FIGS. 7 and 8) that may provide additional friction or gripping force. The clamping device 40 can be configured to pivot in and out of a groove 44 formed in a surface of the medial segment 23. In the embodiment shown in FIG. 7A, a discrete hinge can extend through the clamp 40 and attach to the body 20. In other embodiments, the clamp 40 can be integrally molded to the body 20 in a manner that provides the desired pivoting function as shown in FIG. 7B. For example, the clamp 40 shown in FIG. 7B can be integrally molded to an outer side edge portion of the body 20 without requiring a separate mechanical hinge component. The integrally molded clamp 40 can be biased to a closed (or open position) to allow the clamp 40 to pivot relative to the body of the device 20 between an engaged and disengaged position thereby holding and releasing the cuff 30 during use as desired. The clamp 40 and clamp connection can comprise elastomeric material, and in particular embodiments can comprise a polymer with sufficient structural rigidity to provide the clamping function. Other tensioning, attachment and/or clamping mechanisms and configurations can be used to adjust and/or maintain the desired tension/force.

As shown in FIG. 9, in some embodiments, the support body 20 can include a gauge or feedback mechanism that provides a tactile and/or audible alert when a certain cuff tension is reached or exceeded and/or when a certain occlusion pressure provided by the cuff 30 is reached or exceeded. In operation, a clinician can pull the cuff 30 out of one side of the support body 20 to tighten the cuff 30 against the digit being treated. Generally stated, when a certain external circumferential compression pressure is reached (mmHg) for a given cuff and/or body size, a clinician holding the cuff or proximate the support body 20 is able to feel and/or hear a change that automatically confirms to the clinician that a certain cuff tension and/or cuff pressure has been reached, allowing the clinician to apply a reliable relatively consistent pressure between patients.

Figure 10A:
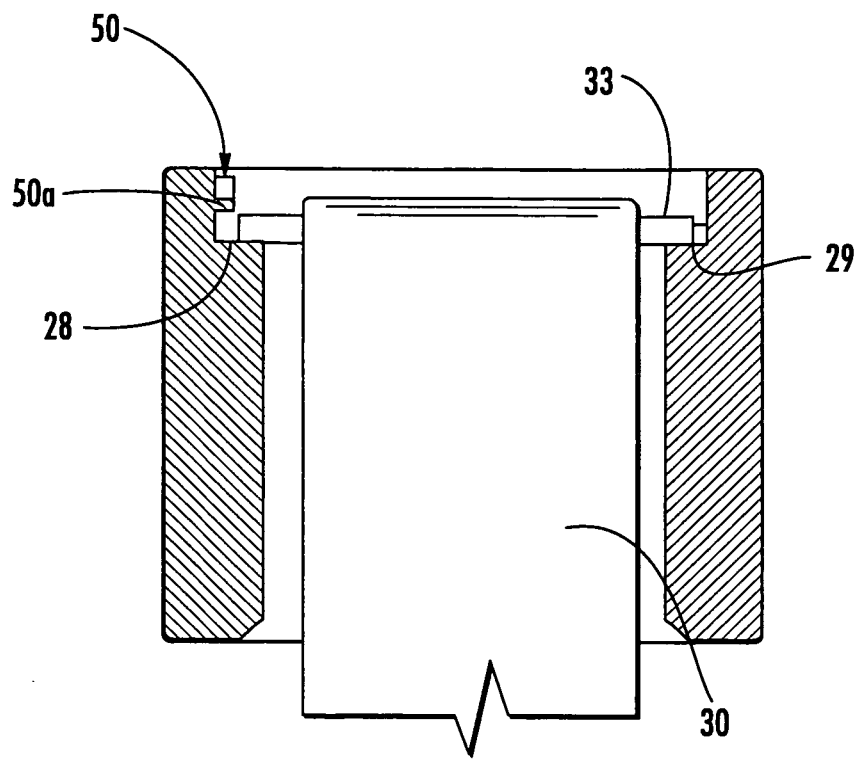
FIG. 10A is an enlarged partial section view of the device shown in FIG. 9, illustrating a configuration of a deformable projection according to embodiments of the present invention.
Figure 10B:
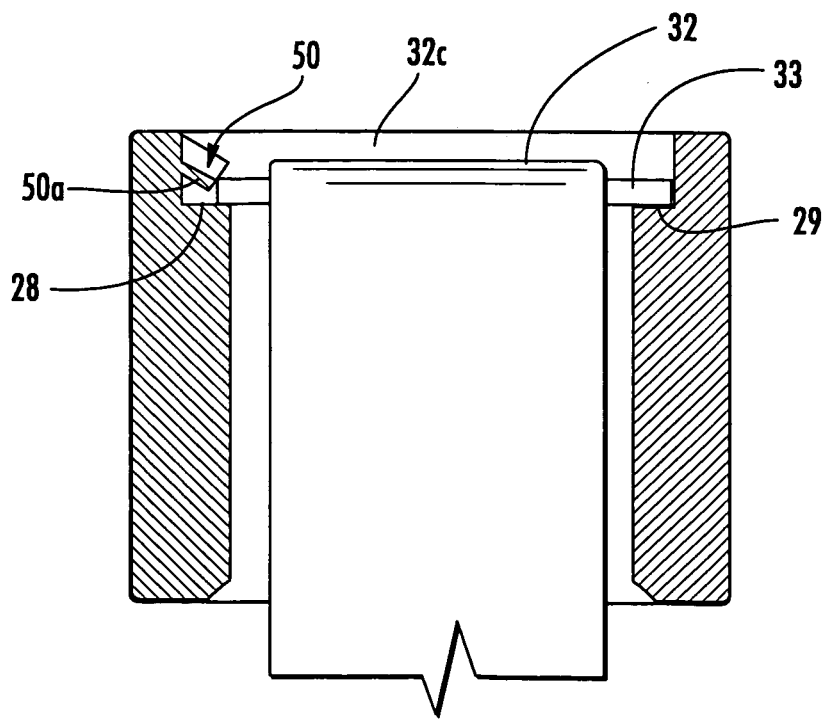
FIG. 10B is an enlarged partial section view of the device shown in FIG. 9, illustrating another configuration of a deformed projection according to embodiments of the present invention.

In the embodiment shown in FIGS. 9, 10A-10D, a deformable projection 50 can be positioned in the first channel 21 of the support body 20. The deformable projection 50 can be configured as a deformable projection arm 50a that is spaced apart from the retaining shoulder 28 as shown in FIGS. 9, 10A and 10B. During operation, the projection arm 50a yields (deforms and/or breaks) to allow the rod 33 to move (typically down) to rest against the retaining shoulder 28 when a certain tension force is exceeded. Thus, the term "deformable" means that the member is configured to deform (typically non-elastically deform) or break when a certain force is exceeded. FIG. 10A illustrates that the arm 50a can break to release the rod 33 while FIG. 10B illustrates that the arm 50a yields but remains intact.

Figure 10C:
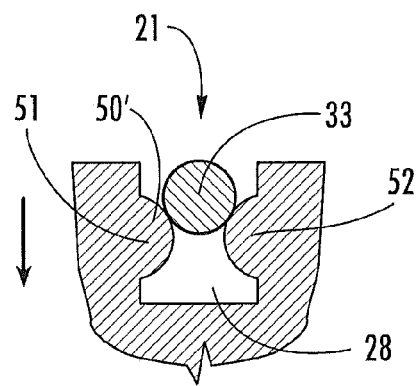
FIG. 10C is an enlarged partial section view of the device shown in FIG. 9 with a different projection configuration.
Figure 10D:
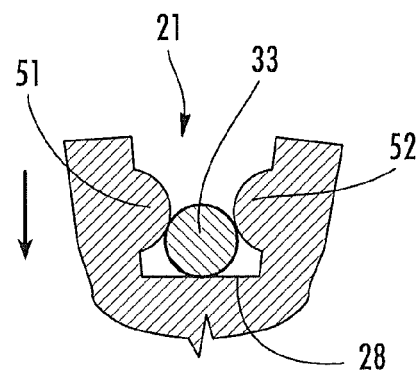
FIG. 10D is an enlarged partial section view of the device shown in FIG. 10C, illustrating the different projection in a deformed configuration according to embodiments of the present invention.

FIG. 10C illustrates that the deformable projection 50' can include two laterally spaced apart deformable projections 51, 52 that impede the movement of the rod 33 until a target tension is exceeded. As shown in FIG. 10D, when sufficient tension is placed on the first end portion of the cuff 32 the rod 33 pushes against the projections 51, 52 to laterally separate the projections 51, 52 a sufficient distance to allow the rod 33 to move down (or up depending on the orientation of the body 20) to the retaining shoulder 28. As before, the deformable projections 51, 52 can be integrally molded to the channel 21 or formed or added as a separate component(s).

The deformable projection 50, 50' can be configured to yield or break at a desired occlusion pressure. That is, the deformable projection 50, 50' can be engineered to yield or break at a calibrated tension or pressure. The deformation can be associated with a tactile feedback (the cuff movement) and/or audible snap that can alert a clinician that a sufficient occlusion pressure has been reached without requiring electronic sensors or peripheral gauges.

In some embodiments, the projection 50, 50' can be integrally molded to the body 20. For example, the projection arm 50a shown in FIG. 9 can be designed in a manner that allows the arm 50 to deform (yield or break) when a desired tension is reached. In other embodiments, the projection 50, 50' can be assembled to the body 20 as a separate component. The projection arm 50a can have a reduced size or scored neck region, comprise a brittle or non-elastic material, and/or have a tension-calibrated shape or other design feature that can allow the projection to yield at a known and/or calibrated tension level to have the projection 50 preferentially deform.

Figure 11A:
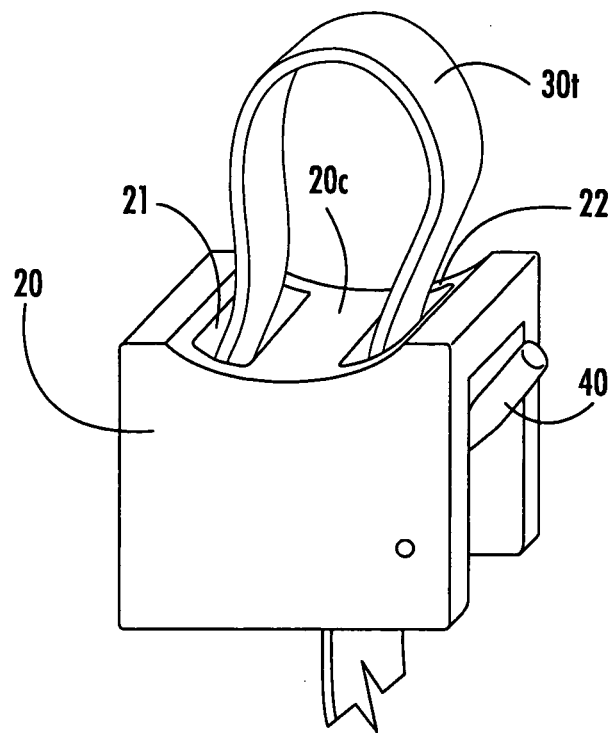
FIGS. 11A-11E are schematic illustrations showing a series of configurations that a cuff can have in a digital tourniquet during use according to embodiments of the present invention.
Figure 11B:
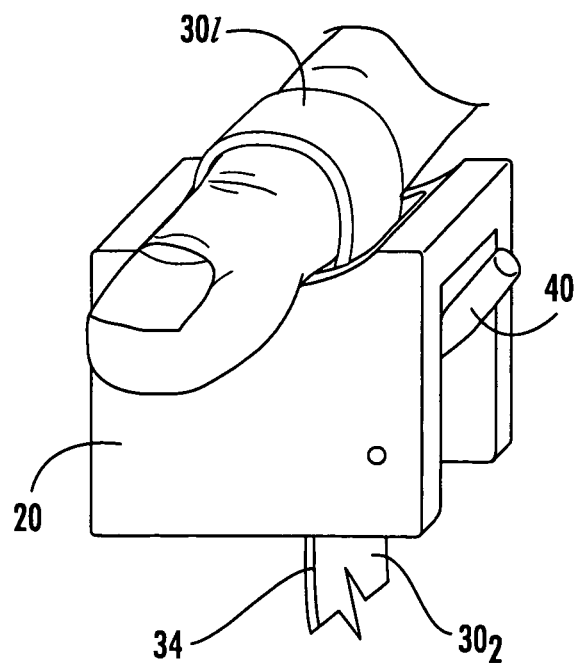
Figure 11C:
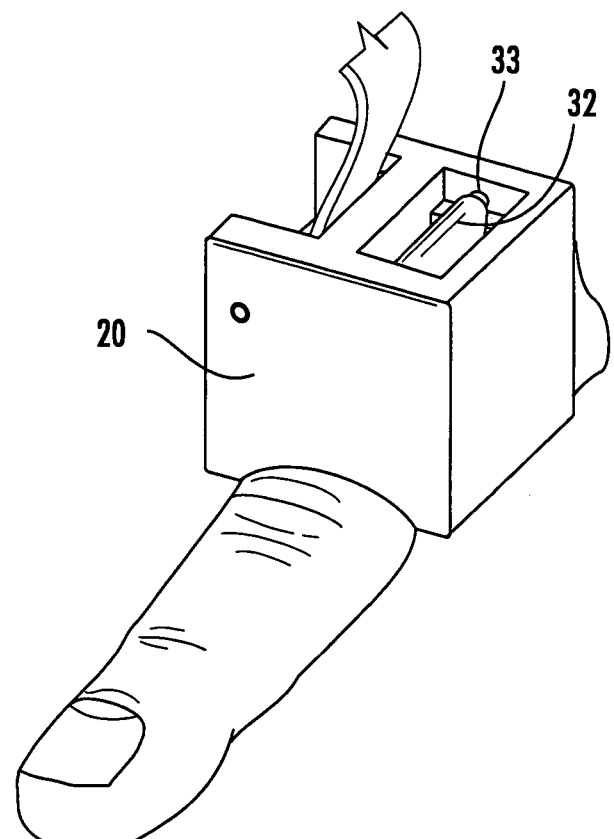

FIGS. 11A-11E illustrate a series of configurations that a cuff 30 and/or tourniquet body 20 may experience in operation according to certain embodiments of the present invention. In use, the tourniquet 10 can be configured with the cuff segment 30s loosely extending above the digit contact surface as shown in FIGS. 11A and 11B and slipped over the digit of interest, typically positioned over the proximal phalanx dorsally. The cuff 30 is then tightened as shown in FIG. 11C to apply occlusion pressure to the digit.

Figure 11D:
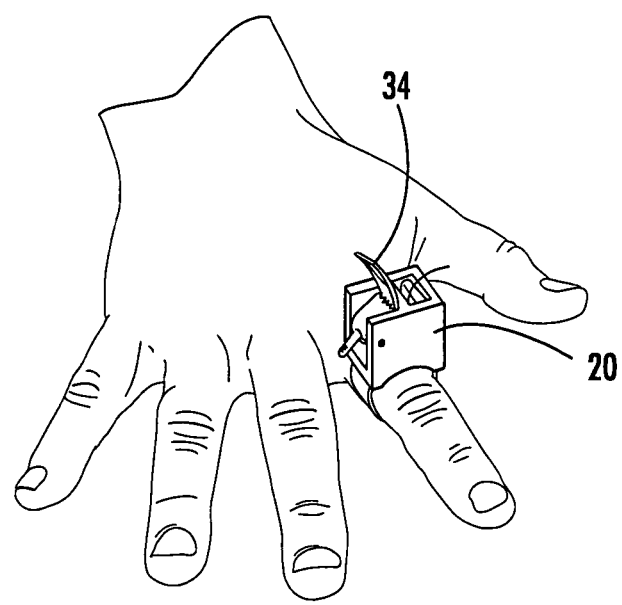
Figure 11E:
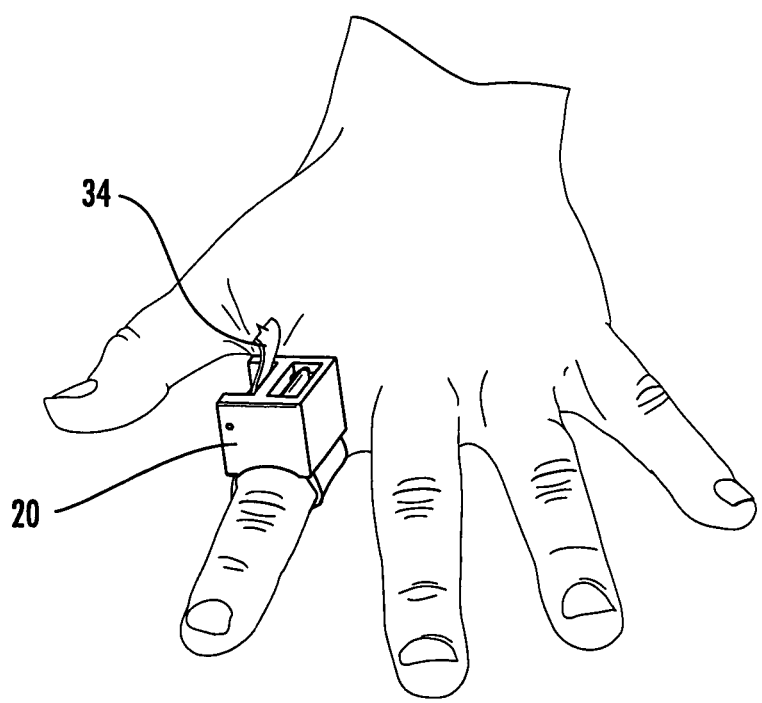

Conventionally, when performing surgery, a clinician sits on the radial (thumb) side of an outstretched hand. Many surgeons are right-handed, and will hold the tourniquet body 20 with their left hand while pulling up on the second end portion of the rubber cuff 34 via the clamp side (shown as side B) with their right hand. During tightening, the clinician can focus on the support body 20 (typically the gauge side (shown as side A)) to be able to stop pulling when the deformable projection yields or breaks. The clinician may want the gauge side (side A) of the support body positioned closest to the thumb for either right or left hand surgery. As shown in FIGS. 11D and 11E, the support body 20 can be selectively oriented by a clinician to position either side A or side B closest to the thumb. The orientation allows for clinician preference so that the clamping/pulling side B (clamping device 40 and cuff side 34) can be easily accessed by the dominant hand to allow for left-handed or right-handed clinicians and/or use on different hands.

It is also noted that although the support body 20 will typically reside above the digit (facing down) with the second end cuff portion 34 extending generally upward and/or outward therefrom, the invention is not limited thereto. For example, the body 20 may be located on a lateral side or under the digit and the cuff 30 pulled sideways and/or downward, as long as the clinician can pull the cuff 30 to tighten the cuff pressure during use.

The cuff 30 can be a generally planar non-inflatable member. The cuff 30 can comprise an elastomeric (typically non-latex) material that is configured to inhibit lateral rolling when tensioned. Other cuff materials may be used as appropriate. For example, the cuffs can comprise synthetic or natural fabric with synthetic or natural fibers or combinations thereof. The cuff 30 can be relatively wide, typically greater than 5 mm, and typically between about 5-15 mm. In some embodiments, the cuff widths can be provided in a range of sizes between about 8-15 mm. The cuff 30 can also be configured to have limited axial stretch (in the length dimension). The cuff 30 may have a resting width and a functional width (when tensioned). The cuff 30 may comprise a flexible substantially inextensible material that is able to generally maintain the resting width when tensioned.

Typically, within practical limits, a larger cuff width is desired (without affecting access to the treatment area) to provide a lower (minimum) occlusion pressure. The minimum finger occlusion pressure is a function of the circumference of the finger and the patient's systolic blood pressure. See, e.g., *New finger cuffs for use with digital tourniquets*, McEwen et al., J. Hand Surg 1988: 13A: 888-892, the contents of which are incorporated by reference herein. It is believed that using the digital tourniquets 10 of the instant invention can reduce occlusive pressures below 50% of the maximum (uncontrolled pressures) that may be generated by either a Penrose drain, a rolled glove finger or rubber band.

Figure 12:
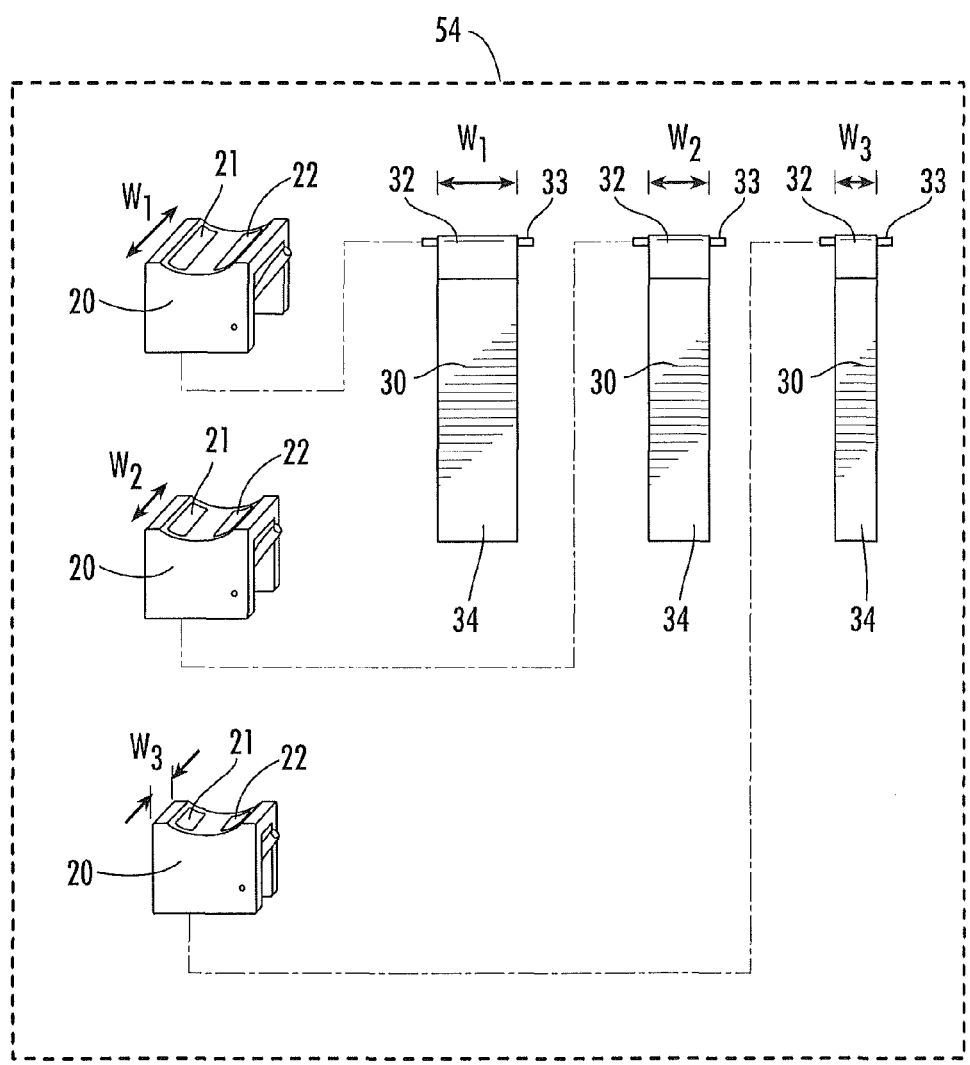
FIG. 12 is a schematic illustration of a set or kit of different tourniquets according to embodiments of the present invention.

FIG. 12 illustrates that the tourniquets 10 can be configured in a plurality of sizes with a corresponding adjustment in the channel sizes 21, 22 and cuff widths 30 to accommodate typical anatomical variations (digit circumference and/or systolic pressure) in the treatment population. Different breaking or yielding strengths of projection(s) 50, 50' can be designed into the different sized bodies 20. Smaller circumference fingers (measured at the middle of the proximal phalanx) may have sufficient occlusion pressure at lower tensions. Alternatively, a plurality of different cuffs 30 of varying cuff widths can be pre-calibrated to be used with a single body 20. In any event, a plurality of different sized tourniquets 10 (bodies 20 and/or cuffs 30) can be provided as a kit to allow a clinician to easily select the optimal one for use in situ, based on one or more patient-specific parameters such as digit circumference. As such, each tourniquet 10 can be sterilized and packaged for single-disposable medical use. Thus, in some embodiments, a corresponding cuff 30 and support body 20 are held in a common sterile package 54. Each body 20 can be individually packaged with or without one or more cuffs in different cuff widths. Alternatively, each body can be individually packaged and a selection of cuffs 30 can be packaged together, as it is anticipated that the cuffs 30 will be cost-effective components, which even if packaged as two or three selectable cuffs for a particular tourniquet body 20, can be disposed of if not selected for use for that patient. Thus, in some embodiments, the kit comprises a plurality of sterile packages 54 that encase a first cuff 30 and first support body 20 and a plurality of sterile packages 54 that encase a second cuff 30 and second support body 20.

The cuffs 30 can be marked with identifying indicia, such as a digit size range and/or target occlusion pressure range when used with a particularly sized body, to reflect the tension and/or projected pressure that will occur using the selected cuff 30 in the body 20 (and potentially related to estimated finger circumference) if the cuff 30 is tensioned to the breaking/yielding point of the projection(s) 50, 50'. The cuff width can affect the applied occlusion pressure as larger cuff widths provide an increased area with reduced pressures for the same applied force P=(F/A). Further lower pressures can be successfully used for larger cuff widths.

Estimates of target pressures using different cuff widths are provided in Table 1. It will be understood that these values can vary based on design considerations, such as cuff thickness, cuff elasticity, cuff width and the finger circumference that a particularly sized tourniquet body/cuff will accommodate. The yielding and/or breaking tension of projection(s) 50, 50' can be correlated to the desired occlusion pressure(s). In some embodiments, the breaking/yielding tension may be a maxima for the cuff and contemplated larger digit size and/or may be averaged for a range of patient sizes.

TABLE 1

PROJECTED CUFF WIDTH V. CONTEMPLATED PRESSURE

| Est. Target Occlusion Pressures | Cuff Width | Finger Circumference |
|---|---|---|
| 225 mmHg-350 mmHg | 10 mm | 50-70 mm |
| 275 mmHg-375 mmHg | 15 mm | 70-90 mm |
| 300 mmHg-350 mmHg | 8 mm | 40-50 mm |

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, if used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A single-use disposable digital tourniquet, comprising:
a substantially rigid block support body defining a curved digit contact outer surface and an opposing outer surface, the curved digit contact surface being concave relative to the block body, the digit contact surface having first and second channel apertures, the digit contact surface being sized and configured to hold a target digit thereagainst, wherein the support body and digit contact surface span at least a major portion of a width of a target digit, the support body comprising first and second spaced apart cuff channels sized and configured to receive a cuff therethrough, wherein the first and second cuff channels extend substantially side-by-side in a depth direction of the support body between the digit contact surface and the opposing outer surface such that, in position, a cuff extends out of the first and second channels of the block body from the first and second channel apertures in the digit contact surface, wherein the block body and cuff cooperate to provide safe occlusive pressures to both sides of the target digit, and wherein, in position, the depth direction is substantially orthogonal to both sagittal and axial directions of a target digit held against the digit contact surface of the support body; and a pivoting clamp that is attached to the block body and is configured with a user accessible member that allows a user to manually pivot the clamp between open and closed positions.

2. A single-use disposable digital tourniquet, comprising: a substantially rigid block support body defining a curved digit contact outer surface and an opposing outer surface, the curved digit contact surface being concave relative to the block body, the digit contact surface having first and second channel apertures, the digit contact surface being sized and configured to hold a target digit thereagainst, wherein the support body and digit contact surface span at least a major portion of a width of a target digit, the support body comprising first and second apart cuff channels sized and configured to receive a cuff therethrough, wherein the first and second cuff channels extend substantially side-by-side in a depth direction of the support body between the digit contact surface and the opposing outer surface such that, in position, a cuff extends out of the first and second channels of the block body from the first and second channel apertures in the digit contact surface, wherein the block body and cuff cooperate to provide safe occlusive pressures to both sides of the target digit, and wherein, in position, the depth direction is substantially orthogonal to both sagittal and axial directions of a target digit held against the digit contact surface of the support body, wherein the first and second cuff channels and corresponding first and second channel apertures are closely spaced in a width dimension corresponding to the sagittal direction with axially extending centerlines of the first and second cuff channels residing between about 1-20 mm apart in the width dimension of the support body and with the channels extending a distance in the axial direction to receive a cuff having a width of between about 8-15 mm, and wherein the digital tourniquet is held in a sterile package for medical use.

3. A digital tourniquet according to claim 1, wherein the curved digit contact surface has a substantially concave shallow profile, the cuff being a non-inflatable elastic cuff, wherein the cuff extends in a single direction through at least one of the first and second cuff channels such that only one end of the cuff resides below the opposing outer surface of the block body away from the digit contact surface whereby the cuff and the block body cooperate to apply the safe occlusive pressure to arteries in opposing sides of a target digit.

4. A digital tourniquet according to claim 3, wherein, the digit support surface includes a center support region, disposed intermediate the first and second cuff channels and the corresponding first and second apertures, that extends between the cuff channels whereby respective portions of the elastic cuff extend substantially vertically in the cuff channels and exit downwardly or upwardly, depending on orientation of the block body on a target digit, from opposing outer edge portions of the support body such that the elastic cuff exits the first cuff channel via the first aperture, snugly travels over a target digit, and returns and enters the second aperture and extends through and exits the second cuff channel to force a target digit tightly against the center support surface.

5. A digital tourniquet according to claim 4, wherein the profile is a substantially arcuate profile with a shallow depth of less than about 5 mm.

6. A digital tourniquet according to claim 4, wherein the profile is sized and configured to receive a minor portion of a target digit therein and to hold a major portion of a target digit above the support body but under a loop of the cuff.

7. A single-use disposable digital tourniquet, comprising: a substantially rigid block support body defining a digit contact outer surface and an opposing outer surface, the curved digit contact surface being concave relative to the block body, the digit contact surface having first and second channel apertures, the digit contact surface being sized and configured to hold a target digit thereagainst, wherein the support body and digit contact surface span at least a major portion of a width of a target digit, the support body comprising first and second spaced apart cuff channels sized and configured to receive a cuff therethrough, wherein the first and second cuff channels extend substantially side-by-side in a depth direction of the support body between the digit contact surface and the opposing outer surface such that, in position, a cuff extends out of the first and second channels of the block body from the first and second channel apertures in the digit contact surface, wherein the block body and cuff cooperate to provide safe occlusive pressures to both sides of the target digit, and wherein, in position, the depth direction is substantially orthogonal to both sagittal and axial directions of a target digit held against the digit contact surface of the support body, wherein the first and second cuff channels extend substantially parallel for at least a major length of the channels, the support body further comprising an anchoring member configured to hold a first end portion of a cuff in the support body first channel and a pivoting clamping member configured to pivot laterally between open and closed positions and to allow a user to manually pivot the clamping member to clamp the cuff against an inner wall of the second channel at a location that is away from the digit support surface proximate the opposing outer surface of the block body, wherein, in operation, the anchoring and clamping members cooperate with the support body to provide a cuff with a nearly closed loop figure at a desired tension over a target digit held on the support body.

8. A single-use disposable digital tourniquet, comprising: a support body comprising a digit support surface and first and second spaced apart cuff channels sized and configured to receive a cuff therethrough, wherein the first and second cuff channels extend under the digit support surface and are closely spaced with at least a portion of each channel being substantially parallel to the other, and wherein the first channel comprises an inner wall with substantially opposing first and second inwardly extending cuff retaining shoulders attached thereto;

a rod sized and configured to reside in the first channel and with a respective one of opposing first and second end portions of the rod configured to reside against a respective one of the cuff retaining shoulders to hold a first end portion of a cuff in the support body first channel;

a clamping member in communication with the second cuff channel configured to hold a portion of the cuff residing below the digit support surface proximate or in the second channel, wherein, in operation, the rod and clamping member cooperate with the support body to provide a cuff with a nearly closed loop figure at a desired tension over a digit held on the support body digit support surface; and at least one deformable member configured to operatively communicate with the rod holding the first end portion of the cuff, the at least one deformable member configured to automatically yield or break when the cuff is tensioned above a target amount to provide a tactile and/or audible alert to a clinician that a target occlusion pressure has been achieved.

9. A digital tourniquet according to claim 1, the first channel comprising a wall with a pair of inwardly extending spaced apart first and second cuff retaining shoulders, the digital tourniquet further comprising a rod that resides against the retaining shoulders and extends across the first channel, the rod configured to hold an end portion of a non-inflatable planar cuff in position in the first channel.

10. A single-use disposable digital tourniquet, comprising:
a non-inflatable planar cuff;
a rod extending across an end portion of the planar cuff;
a support body sized and configured to hold a digit against an upper surface thereof, the support body comprising first and second closely spaced apart cuff channels sized and configured to receive the cuff therethrough, wherein the first channel comprises an inner wall with spaced apart first and second cuff retaining shoulders extending from the wall outwardly across a portion of the first channel, wherein the rod engages the first and second cuff retaining shoulders to hold the rod and end portion of the cuff in position across the first channel, and wherein the first channel further comprises a deformable projection arm extending across a portion of the first channel in advance of the first and/or second cuff retaining shoulder, whereby, in operation, the deformable projection arm deforms allowing at least one end portion of the rod to translate a further distance into the first channel to securely reside against the first and second cuff retaining shoulders when the tourniquet exerts a target tension upon a digit of a patient residing on the support body under the cuff and over the cuff channels thereby providing audible and/or tactile feedback to a user that a desired tourniquet pressure has been reached.

11. A single-use disposable digital tourniquet, comprising:
a substantially rigid block support body defining a curved digit contact outer surface and an opposing outer surface, the curved digit contact surface being concave relative to the block body, the digit contact surface having first and second channel apertures, the digit contact surface being sized and configured to hold a target digit thereagainst, wherein the support body and digit contact surface span at least a major portion of a width of a target digit, the support body comprising first and second spaced apart cuff channels sized and configured to receive a cuff therethrough, wherein the first and second cuff channels extend substantially side-by-side in a depth direction of the support body between the digit contact surface and the opposing outer surface such that, in position, a cuff extends out of the first and second channels of the block body from the first and second channel apertures in the digit contact surface, wherein the block body and cuff cooperate to provide safe occlusive pressures to both sides of the target digit, and wherein, in position, the depth direction is substantially orthogonal to both sagittal and axial directions of a target digit held against the digit contact surface of the support body, wherein the support body is a single-piece molded block body which comprises a polymer material and includes a pivoting clamp attached to the support body proximate the opposing outer surface of the block body to be able to allow a user to pivot the clamp to close against an inner surface of the second channel to contact an inner primary surface portion of a cuff and trap a cuff between the clamp and the inner surface of the second channel and allow the user to pivot the clamp in a reverse direction to release the cuff.

12. A single-use disposable digital tourniquet, comprising:
a substantially rigid block support body defining a curved digit contact outer surface and an opposing outer surface, the curved digit contact surface being concave relative to the block body, the digit contact surface having first and second channel apertures, the digit contact surface being sized and configured to hold a target digit thereagainst, wherein the support body and digit contact surface span at least a major portion of a width of a target digit, the support body comprising first and second spaced apart cuff channels sized and configured to receive a cuff therethrough, wherein the first and second cuff channels extend substantially side-by-side in a depth direction of the support body between the digit contact surface and the opposing outer surface such that, in position, a cuff extends out of the first and second channels of the block body from the first and second channel apertures in the digit contact surface, wherein the block body and cuff cooperate to provide safe occlusive pressures to both sides of the target digit, and wherein, in position, the depth direction is substantially orthogonal to both the sagittal and axial directions of a target digit held against the digit contact surface of the support body, the tourniquet further comprising:
a planar non-inflatable elastomeric cuff having opposing first and second end portions that are slidably insertable through the respective first and second apertures and corresponding first and second channels of the support body so as to extend substantially vertically through the first channel and substantially vertically in a single direction through the second channel to provide the cuff with a cuff intermediate portion that extends outward from the support body digit contact surface and two opposing cuff side portions that extend through respective first and second channels of the support body whereby the cuff compresses the target digit against the digit contact surface of the support body to apply the safe occlusion pressure that is between about 225 mm Hg and 375 mm Hg; and
a rod attached to the first end portion of the cuff, the rod sized and configured to extend across the first channel a distance away from the digit support surface to attach to the support body and secure the rod and the first end portion of the cuff to the support body.

13. A digital tourniquet according to claim 12, wherein the first end portion of the cuff includes a rod channel extending thereacross, the rod channel configured to receive the rod therethrough and hold the cuff in the first channel of the support body at a location proximate the opposing surface of the block body that is away from the digit contact surface.

14. A digital tourniquet according to claim 13, wherein the digit support surface has a shallow curved profile of a depth that is less than about 5 mm sized and configured to hold a target digit thereon so that a digital mid-line of a target digit resides above bounds of the support body, and wherein the opposing outer surface is substantially planar, and wherein the first and second channels have a width that is wider than the width of the cuff.

15. A digital tourniquet comprising:

a substantially rigid block support body comprising first and second spaced apart cuff channels that are closely spaced and extend substantially side-by-side in a depth dimension of the support body, wherein the support body comprises a first digit support surface with first and second cuff apertures spaced apart in a sagittal direction, the first cuff aperture aligned with and merging into the first cuff channel and the second cuff aperture aligned with and merging into the second cuff channel, the digit support surface being concave relative to the block body, wherein, in position, the support body contacts a target digit with the depth dimension being substantially orthogonal to both sagittal and axial directions of the target digit, and wherein the support body digit contact surface is sized and configured to hold at least a major portion of a width of a target digit thereagainst; and a planar non-inflatable elastomeric cuff that is slidably insertable through the first and second apertures into the respective first and second channels of the support body so as to extend substantially vertically through the first channel away from the first surface and substantially vertically in a single direction through the second channel away from the first surface to provide the cuff with two substantially vertically extending portions and an intermediate curvilinear portion that extends outward from the support body first surface to receive a digit through the curvilinear portion, whereby the cuff and support body provide a safe occlusive pressure for the target digit, wherein the second channel includes a pivoting clamp with a user-accessible lever, the clamp attached to the support body proximate the opposing outer surface of the block body, the lever configured to allow a user to pivot the clamp to close against an inner surface of the second channel to contact an inner primary surface portion of the cuff and trap the cuff between the clamp and the inner surface of the second channel and pivot the clamp in a reverse direction to release the cuff, and wherein centerlines of the channels and apertures reside between about 1-20 mm apart, and wherein the cuff has a width of between about 8-15 mm.

16. A digital tourniquet comprising:

a substantially rigid block support body comprising first and second spaced apart cuff channels that are closely spaced and extend substantially side-by-side in a depth dimension of the support body, wherein the support body comprises a first digit support surface with first and second cuff apertures spaced apart in a sagittal direction, the first cuff aperture aligned with and merging into the first cuff channel and the second cuff aperture aligned with and merging into the second cuff channel, the digit support surface being concave relative to the block body, wherein, in position, the support body contacts a target digit with the depth dimension being substantially orthogonal to both sagittal and axial directions of the target digit, and wherein the support body digit contact surface is sized and configured to hold at least a major portion of a width of a target digit thereagainst; and a planar non-inflatable elastomeric cuff that is slidably insertable through the first and second apertures into the respective first and second channels of the support body so as to extend substantially vertically through the first channel away from the first surface and substantially vertically in a single direction through the second channel away from the first surface to provide the cuff with two substantially vertically extending portions and an intermediate curvilinear portion that extends outward from the support body first surface to receive a digit through the curvilinear portion, whereby the cuff and support body provide a safe occlusive pressure for the target digit, wherein the second channel includes a pivoting clamp with a user-accessible lever, the clamp attached to the support body proximate the opposing outer surface of the block body, the lever configured to allow a user to pivot the clamp to close against an inner surface of the second channel to contact an inner primary surface portion of the cuff and trap the cuff between the clamp and the inner surface of the second channel and pivot the clamp in a reverse direction to release the cuff, and wherein the concave surface comprises a shallow concave profile with a depth of less than about 5 mm with a medial closed outer surface portion that separates the first and second cuff apertures and channels.

17. A digital tourniquet according to claim 15, wherein the cuff comprises opposing first and second end portions, the first end portion comprising a rod channel extending thereacross and a rod held therein with opposing end portions of the rod extending beyond bounds of the cuff, and wherein the rod is configured to extend across one of the first and second channels in the support body at a depth dimension that is spaced apart from the first digit support surface of the support body.

18. A digital tourniquet according to claim 17, wherein the support body has a second outer surface opposing the first surface at a depth dimension away from the first surface, the support body further comprising spaced apart first and second rod retaining shoulders in the first channel, the rod configured to rest against the rod retaining shoulders and secure the first end portion of the cuff in the first channel proximate the second outer surface of the support body.

19. A digital tourniquet according to claim 15, wherein the support body has a second outer surface opposing the concave digit support surface wherein the support body further comprises an anchoring member configured to hold a first end portion of a cuff in the support body first channel, and wherein the pivoting clamp is configured to pivot toward the inner surface of the second cuff channel to hold a spaced apart portion of the cuff in or proximate the second channel proximate the second outer surface of the support body, wherein, in operation, the anchoring member and clamp cooperate with the support body to provide a cuff with a turn portion that extends away from the support body and is held at a desired tension over a target digit held on the support body to provide the safe occlusive pressure.

20. A digital tourniquet comprising:

a support body sized and configured to define a digit support surface for a target digit of a patient, the support body comprising first and second spaced apart closely spaced cuff channels that are oriented such that at least a major portion of each cuff channel extends substantially side-by-side downwardly under or upwardly over the digit support surface; and a planar non-inflatable elastomeric cuff that is slidably insertable through the first and second channels of the support body so as to extend through the first channel above and away from the digit support surface, then down and into the second channel to provide a cuff with a curvilinear portion that extends outward from the support body digit support surface, wherein the support body further comprises at least one deformable member configured to operatively communicate with the cuff, the at least one deformable member configured to automatically yield or break when the cuff is tensioned above a target amount to provide a tactile and/or audible alert to a clinician that a target occlusion pressure has been achieved, wherein the support body and cuff are held in a sterile package for surgical use.

21. A digital tourniquet comprising:

a support body comprising first and second spaced apart cuff channels, wherein the support body comprises a first digit support surface that, in position, contacts and holds a target digit, wherein the first and second cuff channels are closely spaced to each other and extend substantially side-by-side under or above the digit support surface through at least a major portion of a depth of the support body, wherein the first channel further comprises spaced apart first and second rod retaining shoulders in the first channel;

a planar non-inflatable elastomeric cuff that is slidably insertable through the first and second channels of the support body so as to extend through the first channel away from the first surface and into the second channel to provide the cuff with a curvilinear portion that extends outward from the support body first surface, wherein the cuff comprises opposing first and second end portions, the first end portion comprising a rod channel extending thereacross; and a rod extending in the rod channel with opposing end portions of the rod extending beyond the bounds of the first end portion of the cuff, the rod configured to rest against the rod retaining shoulders and secure the first end portion of the cuff in the first channel of the support body, wherein the first channel further comprises a deformable projection arm extending across a portion of the first channel in advance of the first and/or second cuff retaining shoulder, wherein, in operation, the rod is configured to press against the projection arm until the arm yields or breaks and allows the rod to move and rest against the retaining shoulders to provide a tactile and/or audible feedback to a clinician that a target occlusion pressure has been achieved, and wherein the digital tourniquet is held in a sterile package for medical use.

22. A digital tourniquet according to claim 15, wherein the support body comprises a molded polymer material.

23. A digital tourniquet according to claim 15, wherein the tourniquet is single-use disposable.

24. A method of applying occlusion pressure to a digit, comprising:

providing a block support body having a digit contact surface and an opposing outer surface, the digit contact surface configured to span at least a major portion of a width of a target digit, the block body also having two substantially parallel spaced apart cuff channels extending substantially vertically therethrough and a substantially planar non-inflatable elastomeric cuff that extends through the first and second channels and out of apertures in the digit contact surface, the cuff having opposing first and second end portions, the first end portion being secured to the support body proximate the first channel with the cuff extending through the second channel in one direction such that the second end portion extends out an aperture in the opposing outer surface, the aperture in the opposing outer surface being aligned with one of the apertures in the digit contact surface;

placing a digit of interest on the digit contact surface of the support body inside a loop portion of the cuff;

pulling the second end portion of the elastomeric cuff to tighten the cuff snugly about at least a major portion of the digit to force the digit against the support body;

pivoting a clamp against a portion of the cuff to clamp the cuff against an inner surface of the second cuff channel proximate the opposing outer surface of the block body to provide a desired safe occlusion pressure to the digit of interest; and automatically providing tactile and/or audible feedback to a user in response to the pulling step when the desired safe occlusion pressure is achieved.

25. A kit of non-inflatable cuffs, a respective cuff adapted to engage a digit tourniquet block support body, the kit comprising a plurality of elongate non-inflatable elastomeric cuffs of different widths, the cuffs having a width of between about 5-15 mm, each cuff having an end portion with a channel configured to accept a rod thereacross, and wherein each cuff comprises a rod extending through the channel for engaging a digit tourniquet block support body.

26. A method according to claim 24, wherein the pulling step comprises pulling the cuff substantially vertically away from the support body at a location that is spaced apart from the digit contact surface in a direction that is substantially aligned with the direction of the second cuff channel in the support body.

27. A method according to claim 24, wherein, in position, when the first end portion of the cuff is attached to the support body inside the first channel, the cuff is configured with a length that is sufficient to extend through the support body first channel, exit the first channel at the first aperture in the digit contact surface and extend outward a distance from the digit contact surface, then enter the second channel of the support body via the second aperture in the digit contact surface and exit an egress portion of the second channel, and wherein the cuff has a width dimension of between 1-20 mm.

28. A method according to claim 24, wherein the digit contacting surface is concave relative to the block body and comprises a center strip at a lowermost portion of the contacting surface that separates the first and second apertures.

29. A method according to claim 28, wherein the support member comprises a shallow curvilinear profile, and wherein the cuff channels have a width that extends in a length (axial) direction of the digit.

30. A method according to claim 24, wherein the support body is configured to be selectively used with a first edge portion facing a finger tip or with the first edge portion facing the hand, and wherein the pivoting step is carried out in response to a user manually moving an externally accessible lever.

31. A kit of digital tourniquets providing for a range of different occlusion pressures, comprising:

a first digital tourniquet substantially rigid block support body having first and second cuff channels with lengths sized to accommodate a non-inflatable elastomeric planar cuff having a first width, the support body having a concave digit support surface that is sized and configured to hold a digit thereon with the cuff extending outwardly therefrom in cooperating engagement with the support body to hold the digit at a desired occlusion pressure, wherein the digit support surface comprises first and second cuff receiving apertures spaced apart in a sagittal direction and having a length that extends in an axial direction, the first aperture aligned with the first cuff channel and the second aperture aligned with the second cuff channel, wherein the first and second closely spaced cuff channels extend substantially side-by-side in a depth direction of the support body, the depth direction being substantially orthogonal to the sagittal and axial directions of the support body; and a second digital tourniquet substantially rigid block support body having first and second cuff channels with lengths sized to accommodate a non-inflatable elastomeric planar cuff having a second width that is greater than the first digital tourniquet cuff first width, the support body having a concave digit support surface that is sized and configured to hold a digit thereon with the cuff extending outwardly therefrom in cooperating engagement with the support body to hold the digit at a desired occlusion pressure, wherein the digit support surface comprises first and second cuff receiving apertures spaced apart in the sagittal direction and having a length that extends in the axial direction, the first cuff aperture aligned with the first cuff channel and the second cuff aperture aligned with the second cuff channel, wherein the first and second closely spaced cuff channels extend substantially side-by-side in a depth direction of the support body, the kit further comprising first and second planar non-inflatable elastomeric cuffs, each having a width between about 1-20 mm and a rod attached to an end portion thereof, wherein the first cuff has a first cuff width configured for insertion into the first support body and the second cuff has a second cuff width that is greater than the first cuff width and is configured for insertion into the second support body.

32. A kit of digital tourniquets providing for a range of different occlusion pressures, comprising:

a first digital tourniquet substantially rigid support body having first and second cuff channels with lengths sized to accommodate a non-inflatable elastomeric planar cuff having a first width, the support body sized and configured to hold a digit thereon with the cuff extending outwardly therefrom in cooperating engagement with the support body to hold the digit at a desired occlusion pressure, wherein the first and second closely spaced cuff channels extend substantially side-by-side in a depth direction of the support body;

a second digital tourniquet substantially rigid support body having first and second cuff channels with lengths sized to accommodate a non-inflatable elastomeric planar cuff having a second width that is greater than the first digital tourniquet cuff first width, the support body sized and configured to hold a digit thereon with the cuff extending outwardly therefrom in cooperating engagement with the support body to hold the digit at a desired occlusion pressure, wherein the first and second closely spaced cuff channels extend substantially side-by-side in a depth direction of the support body; and first and second planar non-inflatable elastomeric cuffs having a width between about 1-20 mm and a rod attached to an end portion thereof, the first cuff having a first cuff width configured for insertion into the first support body and the second cuff having a second cuff width that is greater than the first cuff width and is configured for insertion into the second support body, wherein the first and second support bodies comprise at least one deformable projection member that, in operation, are in communication with a respective cuff and rod held in the support body and configured to deform in response to force applied by the rod upon tensioning of the cuff to allow the rod to translate to a resting secure position and to provide an audible and/or tactile indication to a clinician of when a target occlusion pressure has been reached.

33. A kit according to claim 31, wherein the cuffs comprise opposing first and second end portions, and wherein the first end portion has a rod channel that holds the rod therein.

34. A kit according to claim 33, wherein the rod of each cuff is held in the respective rod channel so that opposing end portions of the rod extend beyond the bounds of the cuff rod channel.

35. A kit according to claim 31, wherein a corresponding cuff and support body are held in a common sterile package.

36. A kit according to claim 35, wherein the kit comprises a plurality of sterile packages that encase the first cuff and first support body and a plurality of sterile packages that encase the second cuff and second support body.

37. A kit according to claim 25, wherein the cuffs are packaged in sterile packages.

38. A digital tourniquet comprising:

a support body sized and configured to define a digit support surface for a target digit of a patient, the support body comprising first and second spaced apart closely spaced cuff channels that are oriented such that at least a major portion of each cuff channel extends substantially side-by-side downwardly under or upwardly over the digit support surface; and a planar non-inflatable elastomeric cuff that is slidably insertable through the first and second channels of the support body so as to extend through the first channel above and away from the digit support surface, then down and into the second channel to provide a cuff with a curvilinear portion that extends outward from the support body digit support surface, wherein the support body further comprises at least one deformable member configured to operatively communicate with the cuff, the at least one deformable member configured to automatically yield or break when the cuff is tensioned above a target amount to provide a tactile and/or audible alert to a clinician that a target occlusion pressure has been achieved, wherein the digit support surface is curved, the tourniquet further comprising at least one rod extending across the first channel and through a first end portion of the cuff, wherein the rod holds the first end portion of the cuff in position in the first cuff channel, and wherein, in operation, the rod communicates with the at least one deformable member to force the deformable member to automatically yield or break when the cuff is tensioned above a target amount to provide the tactile and/or audible alert to a clinician that a target occlusion pressure has been achieved whereby after the deformable member yields or breaks the rod then moves deeper into the first channel to engage rod retaining shoulders projecting from an inner wall of the cuff channel.

39. A single-use disposable digital tourniquet, comprising:

a substantially rigid block support body defining a digit contact outer surface and an opposing upper or lower outer surface, the digit contact surface being concave relative to the block body and sized and configured to hold a digit thereagainst, wherein the digit contact surface comprises first and second cuff apertures spaced apart in a lateral (sagittal) direction, wherein the support body and digit contact surface span at least a major portion of a width of a target digit, the support body comprising first and second spaced apart cuff channels sized and configured to receive a cuff, the first cuff channel aligned with the first cuff aperture and the second cuff aperture aligned with the second cuff channel, wherein the first and second cuff channels extend substantially side-by-side in a depth direction of the support body between the digit contact surface and the opposing outer surface; and a non-inflatable elastomeric cuff having opposing first and second end portions, the first end portion attached to the block support body in the first cuff channel, the cuff extending out of the first cuff aperture and into the second cuff aperture, wherein the cuff extends through the second cuff channel in a single direction so that the second end portion of the cuff resides below the opposing outer surface of the block body, whereby the cuff and the block body cooperate to apply a target safe occlusive pressure to arteries in opposing sides of a target digit, and wherein the cuff and support body are held in a sterile package for medical use;

the tourniquet further comprising a pivoting clamp that is attached to the block body proximate the opposing outer surface of the block body away from the digit contact surface and is configured with a user accessible lever that allows a user to manually pivot the clamp between open and closed positions, the clamp configured to pivot toward an inner wall of the second channel to securely hold a primary surface of the cuff against the inner wall of the second channel in the closed position.

40. A digital tourniquet according to claim 16, wherein the cuff comprises opposing first and second end portions, the first end portion comprising a rod channel extending thereacross and a rod held therein with opposing end portions of the rod extending beyond bounds of the cuff, and wherein the rod is configured to extend across one of the first and second channels in the support body at a depth dimension that is spaced apart from the first digit support surface of the support body.

41. A digital tourniquet according to claim 40, wherein the support body has a second outer surface opposing the first surface at a depth dimension away from the first surface, the support body further comprising spaced apart first and second rod retaining shoulders in the first channel, the rod configured to rest against the rod retaining shoulders and secure the first end portion of the cuff in the first channel proximate the second outer surface of the support body.

42. A digital tourniquet according to claim 16, wherein the support body has a second outer surface opposing the concave digit support surface wherein the support body further comprises an anchoring member configured to hold a first end portion of a cuff in the support body first channel, and wherein the pivoting clamp is configured to pivot toward the inner surface of the second cuff channel to hold a spaced apart portion of the cuff in or proximate the second channel proximate the second outer surface of the support body, wherein, in operation, the anchoring member and clamp-cooperate with the support body to provide a cuff with a turn portion that extends away from the support body and is held at a desired tension over a target digit held on the support body to provide the safe occlusive pressure.

43. A digital tourniquet according to claim 16, wherein the support body comprises a molded polymer material.

44. A digital tourniquet according to claim 16, wherein the tourniquet is single-use disposable.

* * * * *

UNITED STATES PATENT AND TRADEMARK OFFICE
CERTIFICATE OF CORRECTION

PATENT NO. : 8,486,106 B2
APPLICATION NO. : 11/222956
DATED : July 16, 2013
INVENTOR(S) : Warburton Page 1 of 1

It is certified that error appears in the above-identified patent and that said Letters Patent is hereby corrected as shown below:

In the Claims:

Column 11, Claim 2, Line 26: Please correct "and second apart"
to read -- and second spaced apart --

Column 12, Claim 7, Line 13: Please correct "defining a digit"
to read -- defining a curved digit --

Signed and Sealed this
Twenty-seventh Day of May, 2014

Michelle K. Lee
*Deputy Director of the United States Patent and Trademark Office*